US00PP26893P2

(12) United States Plant Patent
de Jong

(10) Patent No.: US PP26,893 P2
(45) Date of Patent: Jun. 28, 2016

(54) ***ASTRANTIA* PLANT NAMED 'STAR OF MAGIC'**

(50) Latin Name: *Astrantia major*
Varietal Denomination: Star of Magic

(71) Applicant: Jacobus Robertus de Jong, Noordwukerhout (NL)

(72) Inventor: Jacobus Robertus de Jong, Noordwukerhout (NL)

( * ) Notice: Subject to any disclaimer, the term of this patent is extended or adjusted under 35 U.S.C. 154(b) by 139 days.

(21) Appl. No.: 13/999,785

(22) Filed: Mar. 21, 2014

(51) Int. Cl.
*A01H 5/02* (2006.01)

(52) U.S. Cl.
USPC ..... Plt./408

(58) Field of Classification Search
USPC ..... Plt./408
See application file for complete search history.

*Primary Examiner* — Keith Robinson
(74) *Attorney, Agent, or Firm* — Penny J. Aguirre

(57) ABSTRACT

A new cultivar of *Astrantia* 'Star of Magic' that is characterized by its foliage that is variegated with white and green with the variegation retained throughout the summer, its young foliage that is tinged with purple-red, its inflorescences that are purple-red in color, and its two blooming periods; blooming in May to June and then again in September to October in The Netherlands.

2 Drawing Sheets

Botanical classification: *Astrantia major.*
Cultivar designation: 'Star of Magic'.

BACKGROUND OF THE INVENTION

The present invention relates to a new and distinct cultivar of *Astrantia*, botanically known as *Astrantia major* 'Star of Magic', and will be referred to hereafter by its cultivar name, 'Star of Magic'. 'Star of Magic' represents a new herbaceous perennial grown for landscape use.

The new cultivar, 'Star of Magic', was discovered by the Inventor in the summer of 2006 as a naturally occurring branch mutation of *Astrantia* 'Star of Beauty' (not patented) in his trial garden in De Hoef, The Netherlands.

Asexual propagation of the new cultivar was first accomplished by division by the Inventor in the summer of 2006 in Noordwijkerhout, The Netherlands. Asexual propagation by division and tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Star of Magic' as a unique cultivar of *Astrantia.*

1. 'Star of Magic' exhibits foliage that is variegated with white and green with the variegation retained throughout the summer.
2. 'Star of Magic' exhibits young foliage that is tinged with purple-red.
3. 'Star of Magic' exhibits inflorescences that are purple-red in color.
4. 'Star of Magic' exhibits two blooming periods, blooming in May to June and then again in September to October in The Netherlands.

The parent plant of 'Star of Magic', 'Star of Beauty', differs from 'Star of Magic' in having foliage that is not variegated. 'Star of Magic' can be most closely compared to the *Astrantia* cultivars 'Sunningdale Variegated' (not patented) and 'Star of Summer' (not patented). 'Sunningdale Variegated' is similar to 'Star of Magic' in having foliage that is variegated. 'Sunningdale Variegated' differs from 'Star of Magic' in having inflorescences that are pale pink to whitish in color, in having foliage that loses its variegation during the summer and turns solid green in color, and in having young foliage that is not purple-red. 'Star of Summer' is similar to 'Star of Magic' in having purple-red inflorescences, but differs from 'Star of Magic' in having foliage that is not variegated.

BRIEF DESCRIPTION OF THE DRAWING

The accompanying colored photographs illustrate the overall appearance and distinct characteristics of the new *Astrantia*. The photographs were taken of eighteen month-old plants of 'Star of Magic' as field grown in De Hoef, The Netherlands (place in a container for the photographs).

The photograph in FIG. 1 provides a side view of a plant of 'Star of Magic' in bloom.

Figure 1:
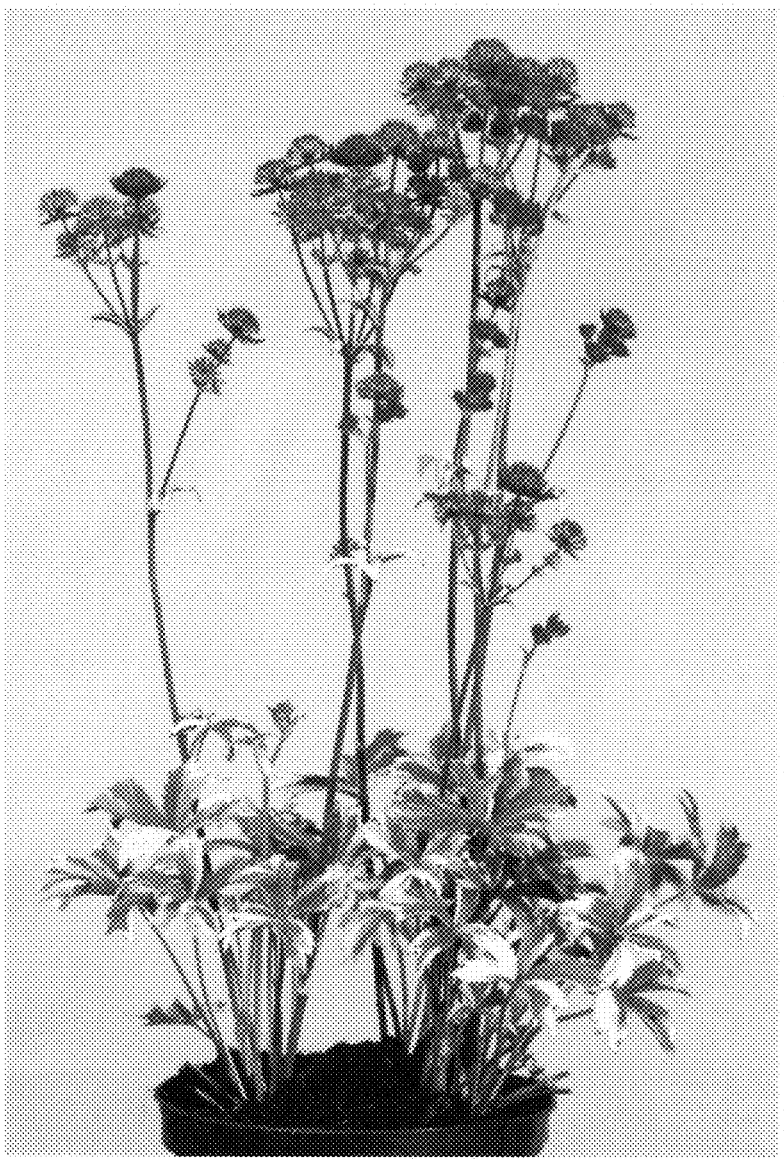
Figure 2:
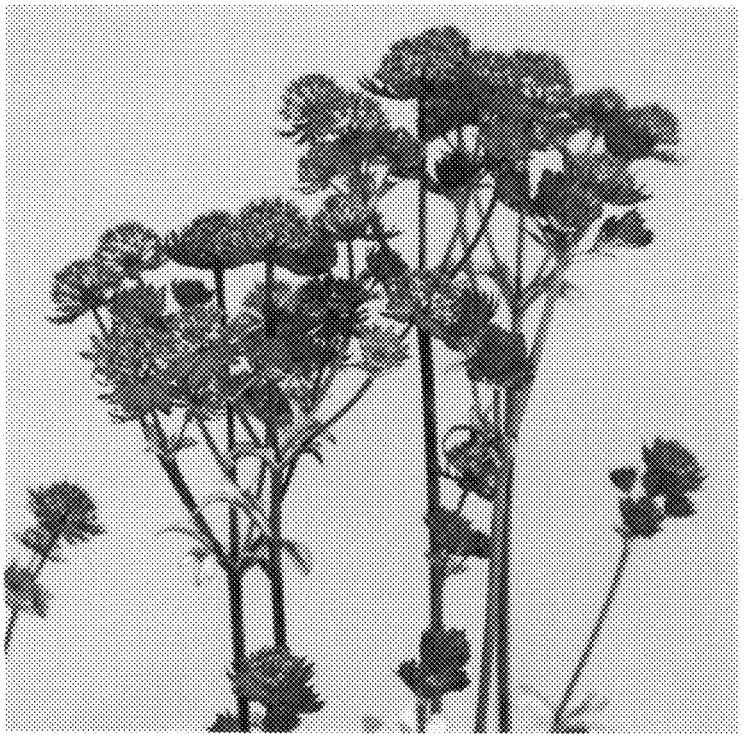

The photograph in FIG. 2 provides a close-up view of the inflorescences of 'Star of Magic'.

Figure 3:
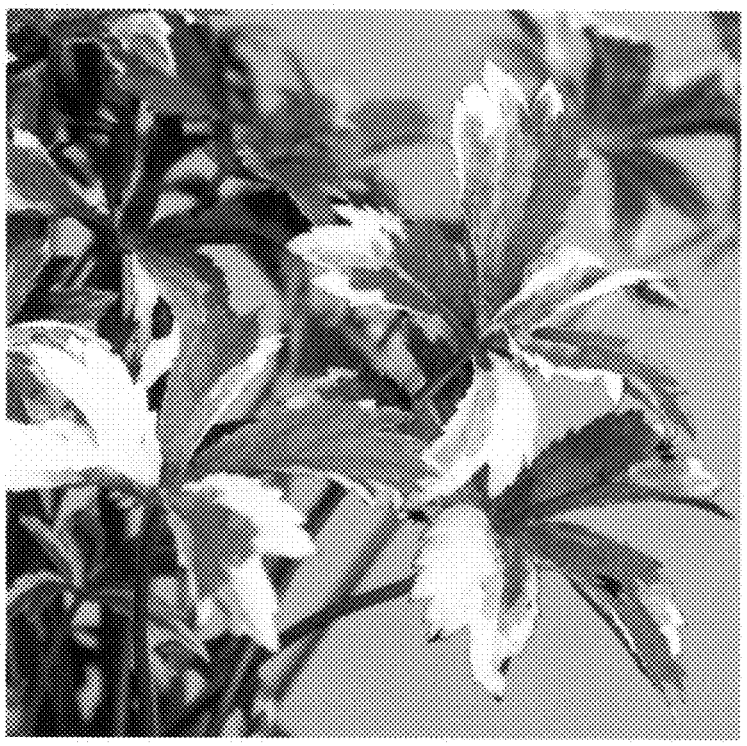

The photograph in FIG. 3 provides a close-up view of the foliage of 'Star of Magic'.

The colors in the photograph may differ slightly from the color values cited in the detailed botanical description, which accurately describe the colors of the new *Astrantia.*

DETAILED BOTANICAL DESCRIPTION

The following is a detailed description of eighteen-month-old plants of the new cultivar as field grown in De Hoef, Netherlands. Plants were grown under average day temperatures ranging from 13° to 27° C. and average night temperatures of 3° to 15° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*.—Herbaceous perennial.

*Blooming period.*—May to June and again in September to June in De Hoef, The Netherlands.

*Plant habit.*—Basal rosette with erect flowering stems.

*Height and spread.*—Reaches 55 to 65 cm in height and 25 to 45 cm in spread.

*Cold hardiness.*—At least to U.S.D.A Zone 6.

*Disease resistance.*—Not more susceptible to pests and diseases than other *Astrantia* varieties.

*Root description.*—Fibrous and fine, 177A in color.

*Root habit.*—Freely branching and dense.

*Propagation.*—Tissue culture or division.

*Growth rate.*—Moderate.

Stem description:

*Stem shape.*—Round.

*Stem color.*—146A and 147A, 146A towards base.

*Stem size.*—Average of 32.5 cm in length (excluding inflorescence) and 4 mm in diameter.

*Stem surface.*—Un-deeply ribbed vertically.

*Stem texture.*—Slightly glossy.

*Stem strength.*—Strong.

*Branching habit.*—Stems grow freely from basal rosette, an average of 8 flowering stems.

*Internode length.*—Average of 11.1 cm.

Foliage description:

*Leaf division.*—Simple.

*Leaf shape.*—Palmately parted, reniform in outline.

*Leaf base.*—Hastate, basal lobes of each leaf slightly overlapping.

*Leaf apex.*—Acute.

*Leaf margin.*—Biserrate, teeth aristate, average length of teeth 1 mm, color of the teeth 200A, tips are N170B to N170C.

*Leaf venation.*—Laciniate in pattern, venation matches the leaf color.

*Leaf arrangement.*—Basal rosette, one stem leaf per stem if present.

*Leaf surface.*—Upper and lower surface; glabrous and very slightly glossy.

*Leaf color.*—Young upper surface 138A, marbled 145B to 145C, irregular margins 154D and 1C to 1D, margins tinged 187C to 187D, young lower surface 138B, irregular margins 5D, outer margins tinged 187C to 187D, mature upper surface; 137A and N137D, with 145C and 147D, irregular margins 5D and 160D, outer margins tinged 200B, mature lower surface 147B, irregular margins 4D, outer margins tinged 200B, variegation is retained throughout the summer.

*Leaf size.*—Basal leaves average 8.4 cm in length and 9.7 cm in width, stem leaves average 6.3 cm in length and 7.2 cm in width.

*Leaf number.*—1 stem leaf per stem and average of 38 basal leaves per plant.

*Petiole.*—Stem leaves; average of 5.8 cm in length and 2 mm in diameter, both sides are 143A in color with upper side streaked with 155A, sheath an average of 3.4 cm in length and 5 mm in width, 157C to 157D in color and blotched with 143A to 143B, basal leaves; average 16.8 cm in length and 3 mm in diameter, both surfaces are 143A in color with upper surface streaked with 155A.

Flower description:

*Inflorescence type.*—Compound umbel.

*Lastingness of inflorescence.*—Average of 2 weeks, self cleaning.

*Inflorescence size.*—Terminal; average of 14.1 cm in height (including peduncle) and 11.5 cm in width, umbel; average of 2 cm in height and 3.7 cm in width.

*Inflorescence fragrance.*—Strong, sweet and pleasant.

*Flower number.*—Average of 75 per umbel, average of 13 umbels per compound umbel, average of 525 flowers per flowering stem.

*Flower form.*—Single, campanulate.

*Flower aspect.*—Upright and upright-outward.

*Flower bud size.*—Average of 1.75 mm in length, average of 1.5 mm in diameter.

*Flower bud color.*—71A, lower half 145C.

*Flower bud shape.*—Obovate with flattened apex.

*Flower size.*—Average of 3 mm in diameter and 8 mm in height.

*Petal number.*—5.

*Petal shape.*—Narrow ovate, incurved.

*Petal color.*—When opening upper and lower surfaces; 75C to 75D, mid section N74D, when fully open upper and lower surfaces; 75D, mid section N74D.

*Petal surface.*—Matte and glabrous on both surfaces.

*Petal margins.*—Entire.

*Petal apex.*—Narrowly acute.

*Petal size.*—Average of 2 mm in length and 1 mm in width.

*Calyx form.*—Rotate, held upright.

*Calyx size.*—Average of 2 mm in length and 2 mm in diameter.

*Sepal number.*—5.

*Sepal shape.*—Narrow ovate.

*Sepal margin.*—Entire.

*Sepal size.*—Average of 2 mm length and 0.8 mm in width.

*Sepal surface.*—Matte and glabrous on both surfaces.

*Sepal apex.*—Narrowly acute.

*Sepal base.*—Cuneate, fused.

*Sepal color.*—Immature upper and lower surfaces; 61A, mature upper and lower surfaces; 60C to 60D.

*Peduncle size.*—Average of 12.1 cm in length and 2 mm in diameter.

*Peduncle strength/aspect.*—Strong, terminals held upright, secondary held at an average of 40° from stem.

*Peduncle color.*—147A and 203A.

*Peduncle surface texture.*—Slightly glossy.

*Pedicel size.*—Up to 7 mm in length and 0.2 mm in width.

*Pedicel strength/aspect.*—Strong, terminal held upright, central flowers straight upright, outer flowers held at 80° from stem.

*Pedicel color.*—70A.

*Pedicel surface texture.*—Slightly glossy.

*Inflorescent leaves.*—About 20 per inflorescence, about 1.9 cm in length and 4 mm in width, narrow elliptic in shape, acute apex, attenuate base, entire margins, matte and glabrous surfaces, color of upper surface; 71A, color of lower surface; between 71A and N79B.

Involucral bracts:

*Bract number.*—About 20 per umbel.

*Bract shape.*—Narrow elliptic.

*Bract size.*—About 1.9 cm in length and 4 mm in width.

*Bract color.*—Color of upper surface; 71A, color of lower surface; between 71A and N79B.

*Bract texture.*—Matte and glabrous.

*Bract apex.*—Acute.

*Bract base.*—Attenuate.

*Bract margins.*—Entire.

Reproductive organs:

*Gynoecium.*—2 pistils, about 3.2 mm in length, stigma is club-shaped and 63A in color, style is about 3 mm in length, 63A to 63B in color with base 155C, ovary is 147D in color, 1 mm in length, 0.5 mm in diameter.

*Androcoecium.*—5 stamens, anthers are dorsifixed, elliptic in shape, about 0.5 mm in length and 187A in color, filament is 3 mm in length and N74D in color, pollen is low in quantity and 156D in color.

*Fruit/seeds.*—No fruit set (or seeds) have been observed to date.

It is claimed:

1. A new and distinct cultivar of *Astrantia* plant named 'Star of Magic' as herein illustrated and described.

* * * * *